Figure 1:
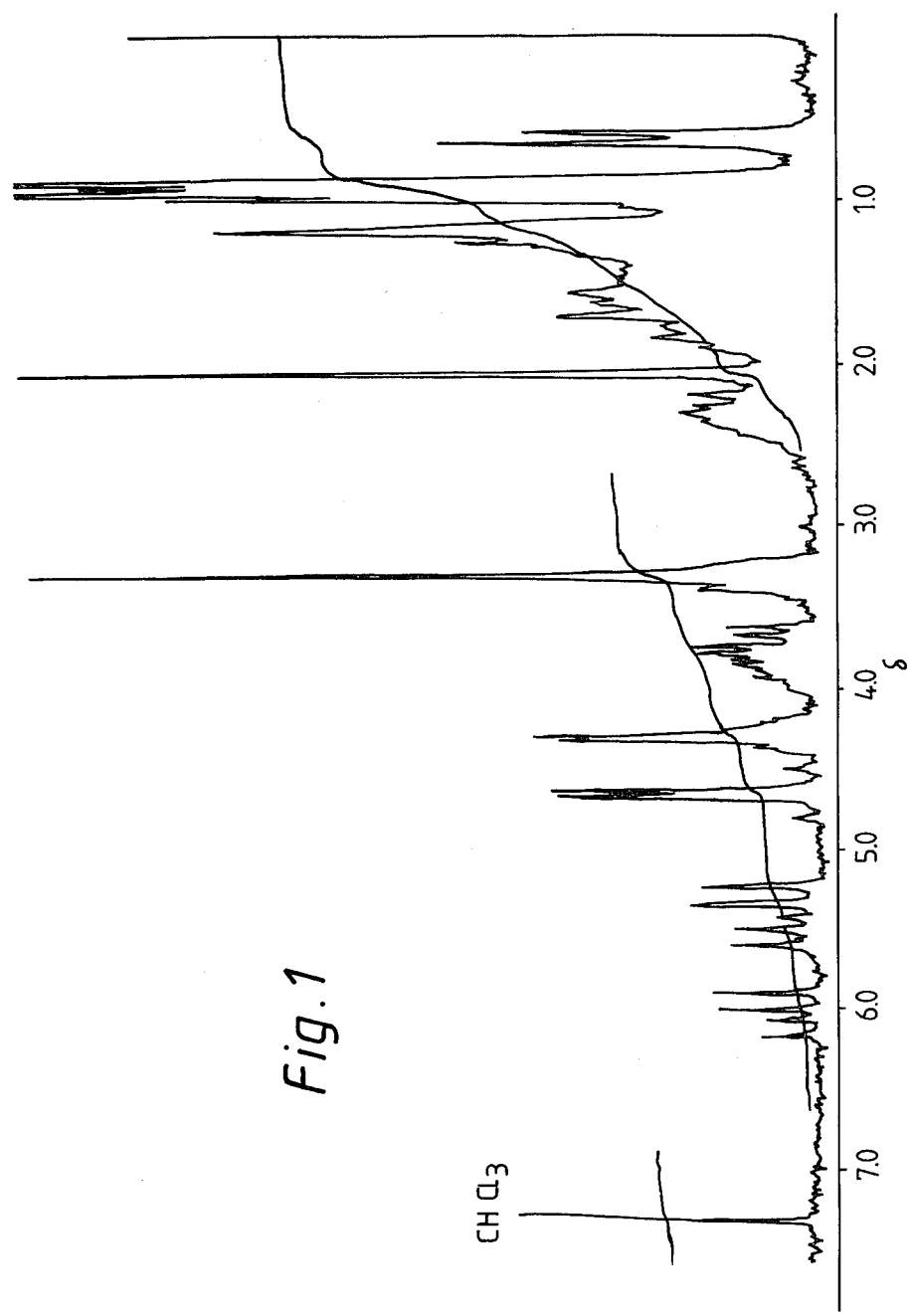

United States Patent [19]

Davies et al.

[11] 4,443,471

[45] Apr. 17, 1984

[54] DERIVATIVES OF M.139,603 USEFUL AS GROWTH PROMOTERS

[75] Inventors: David H. Davies; Michael J. Smithers, both of Macclesfield, England

[73] Assignee: Imperial Chemical Industries PLC, London, England

[21] Appl. No.: 390,773

[22] Filed: Jun. 21, 1982

[30] Foreign Application Priority Data

Jul. 16, 1981 [GB] United Kingdom ................. 8122027
Jul. 20, 1981 [GB] United Kingdom ................. 8122307

[51] Int. Cl.³ ................. C07D 407/14; A61K 31/365; A61K 31/71
[52] U.S. Cl. ................................. 424/279; 549/313; 549/318
[58] Field of Search ......................... 542/430; 424/279

[56] References Cited

FOREIGN PATENT DOCUMENTS 2027013 2/1980 United Kingdom .

*Primary Examiner*—Norma S. Milestone
*Attorney, Agent, or Firm*—Cushman, Darby & Cushman

[57] ABSTRACT

Novel ether, ester, urethane, thiourethane and carbonate derivatives of the ruminant growth promoters, M.139,603, M.139,603-adlehyde and oxime etc. derivatives thereof, all of which are effective in reducing the proportion of methane produced by ruminal fermentation, and increasing the proportion of propionic acid at the expense of acetic acid in the rumen contents; together with processes for their manufacture, compositions containing them, and their use in increasing growth and/or feed efficiency in ruminant animals.

6 Claims, 1 Drawing Figure

DERIVATIVES OF M.139,603 USEFUL AS GROWTH PROMOTERS

This invention relates to ether, ester, urethane and other derivatives of the animal growth promoter known as M.139,603. These derivatives are effective in reducing the proportion of methane produced by ruminal fermentation, and increasing the proportion of propionic acid in rumen fluid, and are therefore believed to possess growth promoting properties in ruminants, it being well known that other chemical compounds which reduce methane and increase propionic acid levels in the rumen result in increased growth rates when fed to ruminants such as cattle and sheep.

The compound known as M.139,603, which is a metabolite obtained from the aerobic culture of *Streptomyces longisporoflavus*, is described and claimed in European Patent Publication No. 70622 A1 and United Kingdom Patent Specification No. 2,027,013 A, and has the structure I, $R^1$=methyl, $R^2$=hydroxymethyl.

The invention provides a derivative of M.139,603 of the formula:

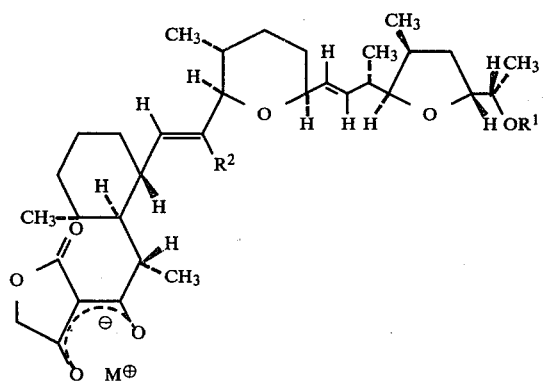

wherein:

$M^+$ is an alkali metal, alkaline earth metal, ammonium, alkylammonium or hydroxyalkylammonium cation;

$R^1$ is a hydrogen atom, an alkyl radical or an optionally substituted phenylalkyl radical; and $R^2$ is a formyl, iminomethyl, hydroxyiminomethyl or aminomethyl radical, or a radical of the formula —CH:$NR^3$, —CH:$NOR^4$ or —$CH_2NR^5R^6$ wherein $R^3$, $R^4$, $R^5$ and $R^6$ may each be an alkyl or an optionally substituted phenyl or phenylalkyl radical; or a radical of the formula —$CH_2OR^7$ wherein $R^7$ is an alkyl, alkenyl, alkynyl, alkoxycarbonyl or alkylaminoalkyl radical or an optionally substituted phenylalkyl radical; or a radical of the formula —$CH_2O.COR^8$ wherein $R^8$ is an alkyl, cycloalkyl, (cycloalkyl)alkyl, halogenoalkyl, hydroxyalkyl, alkoxyalkyl, aminoalkyl, mono- or di-alkylaminoalkyl, alkoxycarbonylalkyl, carboxyalkyl, carbamoylalkyl, N-alkylcarbamoylalkyl, N,N-dialkylcarbamoylalkyl or optionally substituted phenyl, naphthyl or phenylalkyl radical; or a radical of the formula —$CH_2O.CO.COR^9$ wherein $R^9$ is an amino, mono- or di-alkylamino, alkoxy or optionally substituted phenyl, naphthyl or phenylalkyl radical; or a radical of the formula —$CH_2O.CX.NR^{10}R^{11}$ wherein X is an oxygen or sulphur atom and $R^{10}$ and $R^{11}$, which may be the same or different, are each a hydrogen atom, an alkyl radical or an optionally substituted phenyl, naphthyl or phenylalkyl radical; or, when $R^1$ is a hydrogen atom or an alkyl radical of 2 or more carbon atoms or an optionally substituted phenylalkyl radical, $R^2$ is a hydroxymethyl radical, and wherein each alkyl, alkenyl or alkynyl radical contains up to 6 carbon atoms, and wherein, in each complex radical containing an alkyl part, the said alkyl part contains 1 to 6 carbon atoms, and wherein each cycloalkyl radical or cycloalkyl part of a (cycloalkyl)alkyl radical contains 3 to 7 carbon atoms.

A particular value for any of $R^1$, $R^2$, $R^3$, $R^4$, $R^5$, $R^6$, $R^7$, $R^8$, $R^9$, $R^{10}$ and $R^{11}$ when it is an alkyl radical, or when it is a complex radical containing an alkyl part, is, for example, such an alkyl radical which contains 1 to 3 carbon atoms, or such a complex radical wherein the alkyl part contains 1 to 3 carbon atoms.

A particular optional substituent in $R^1$, $R^3$, $R^4$, $R^5$, $R^6$, $R^7$, $R^8$, $R^9$, $R^{10}$ or $R^{11}$ when any of them is an optionally substituted phenyl, naphthyl or phenylalkyl radical is, for example, a halogen atom, a nitro, cyano or hydroxy radical, or an alkyl, alkoxy, halogenoalkyl, halogenalkoxy, alkylamino, dialkylamino or alkanoylamino radical, for example, such a radical of up to 8 carbon atoms, preferably of up to 4 carbon atoms.

A particular value for $R^7$ when it is an alkenyl or alkynyl radical is, for example, such a radical of 2 or 3 carbon atoms.

Particular cations $M^+$ are, for example, the sodium, lithium, potassium, calcium, magnesium, zinc, ammonium, mono-, di-, tri- and tetra-alkylammonium ions wherein each alkyl is of 1 to 10 carbon atoms, and mono-, di- and tri-(hydroxyalkyl)ammonium ions wherein each hydroxyalkyl is of 1 to 10 carbon atoms.

Particular compounds of the invention which are preferred for increasing the proportion of propionic acid in rumen fluid are those compounds of the formula I wherein:

$R^1$ is hydrogen and $R^2$ is hydroxymethyl;
$R^1$ is methyl and $R^2$ is formyl;
$R^1$ is methyl and $R^2$ is methoxymethyl;
$R^1$ is methyl and $R^2$ is propargyloxymethyl;
$R^1$ is methyl and $R^2$ is benzoyloxymethyl;
$R^1$ is methyl and $R^2$ is 2-bromobenzoyloxymethyl;
$R^1$ is methyl and $R^2$ is chloroacetoxymethyl;
$R^1$ is methyl and $R^2$ is ethoxalyloxymethyl; and
$R^1$ is methyl and $R^2$ is N-methylthiocarbamoyloxymethyl.

The compounds of the invention may be prepared by processes which are known in themselves for the manufacture of chemically analogous compounds. Thus, the following processes are provided as a further feature of this invention:

(a) for those compounds wherein $R^2$ is a radical of the formula —$CH_2OR^7$ as defined above, the reaction of a compound of the formula I wherein $R^1$ has any of the meanings defined above and $R^2$ is a hydroxymethyl radical, with a compound of the formula $R^7Z$, wherein $R^7$ has the meaning defined above and Z is a leaving group, for example a halogen atom, such as chlorine or bromine, or a mesyl or tosyl group, in the presence of a strong base, for example sodium hydride or a sodium lower-alkoxide such as sodium methoxide or sodium ethoxide;

(b) for those compounds wherein $R^1$ is other than hydrogen, and $R^2$ is a radical of the formula —$CH_2O$.-

$COR^8$ or $-CH_2O.CO.COR^9$ as defined above, the reaction of a compound of the formula I wherein $R^1$ is an alkyl or optionally substituted phenylalkyl radical and $R^2$ is a hydroxymethyl radical, with an acylating agent derived from a carboxylic acid of the formula $R^8.COOH$ or $R^9CO.COOH$ wherein $R^8$ and $R^9$ have the meanings defined above, for example an acyl halide, such as the chloride, bromide or iodide, an acid anhydride or a mixed anhydride;

(c) for those compounds wherein $R^1$ is other than hydrogen, and $R^2$ is a radical of the formula $-CH_2O.COR^8$ or $-CH_2O.CO.COR^9$ as defined above, the reaction of a compound of the formula I wherein $R^1$ is an alkyl or optionally substituted phenyl or phenylalkyl radical and $R^2$ is a hydroxymethyl radical with a carboxylic acid of the formula $R^8.COOH$ or $R^9CO.COOH$ in the presence of a carbodi-imide, for example dicyclohexylcarbodi-imide;

(d) for those compounds wherein $R^2$ is a radical of the formula $-CH_2O.COR^8$ in which $R^8$ is a hydroxyalkyl radical, the reaction of a compound of the formula I wherein $R^2$ is a radical of the formula $-CH_2O.COR^8$ in which $R^8$ is an (t-alkoxy)alkyl radical with an acid, for example ethanolic hydrogen chloride;

(e) for those compounds wherein $R^2$ is a radical of the formula $-CH_2O.COR^8$ in which $R^8$ is an alkylaminoalkyl or dialkylaminoalkyl radical, the reaction of the corresponding aminoalkyl compound with an alkyl halide, for example an alkyl bromide or alkyl iodide;

(f) for those compounds wherein $R^2$ is a radical of the formula $-CH_2O.COR^8$ in which $R^8$ is an alkoxycarbonylalkyl radical, the reaction of the corresponding carboxyalkyl compound with a diazoalkane, or of a salt of the corresponding carboxyalkyl compound with an alkyl halide, for example an alkyl bromide or alkyl iodide;

(g) for those compounds wherein $R^2$ is a radical of the formula $-CH_2O.COR^8$ in which $R^8$ is a carbamoylalkyl, N-alkylcarbamoylalkyl or N,N-dialkylcarbamoylalkyl radical, the reaction of a corresponding carboxyalkyl or alkoxycarbonylalkyl compound with ammonia or a mono- or di-alkylamine respectively;

(h) for those compounds wherein $R^2$ is a radical of the formula $-CH_2O.CO.COR^9$ in which $R^9$ is an amino, monoalkylamino or dialkylamino radical, the reaction of a corresponding compound wherein $R^9$ is a hydroxy or alkoxy radical with ammonia or a mono- or di-alkylamine respectively;

(i) for those compounds wherein $R^2$ is a radical of the formula $-CH_2O.CX.NR^{10}R^{11}$ wherein $R^{10}$ is a hydrogen atom and X and $R^{11}$ have the meanings defined above, the reaction of a corresponding compound of the formula I in which $R^2$ is a hydroxymethyl radical with an isocyanate or isothiocyanate of the formula $R^{11}.NCX$;

(j) for those compounds wherein $R^2$ is a radical of the formula $-CH_2O.CX.NR^{10}R^{11}$ wherein X has the meanings defined above and either one or both of $R^{10}$ and $R^{11}$ is other than a hydrogen atom, the reaction of a corresponding compound wherein either or both of $R^{10}$ and $R^{11}$ is a hydrogen atom with a halogen compound $R^{10}$.halide or $R^{11}$.halide;

(k) for those compounds wherein $R^2$ is a formyl radical, the oxidation of the corresponding compound wherein $R^2$ is a hydroxymethyl radical, for example with activated manganese dioxide;

(l) for those compounds wherein $R^2$ is an iminomethyl or hydroxyiminomethyl radical or a radical of the formula $-CH:NR^3$ or $-CH:NOR^4$, the reaction of the corresponding compound wherein $R^2$ is a formyl radical with ammonia, hydroxylamine, an amine $R^3NH_2$ or an alkoxyamine $R^4O.NH_2$ respectively;

(m) for those compounds wherein $R^2$ is a radical of the formula $-CH_2NR^5R^6$, or is an aminomethyl radical, the reduction, for example with a borohydride such as sodium borohydride, of a corresponding compound wherein $R^2$ is a radical of the formula $-CH:NR^5$ or $-CH:NR^6$ or wherein $R^2$ is an iminomethyl radical;

(n) for the compound wherein $R^1$ is a hydroxy radical and $R^2$ is a hydroxymethyl radical, the culturing of *Streptomyces longisporoflavus* NCIB 11426 or a variant or mutant thereof in an aqueous nutrient medium, containing a source of assimilable carbon, under shaken aerobic conditions at a temperature of between 22° and 32° C., extracting the fermentation mixture with a water-immiscible organic solvent, and isolating from the organic extract the product which has $R_F=0.43$ on thin-layer chromatography on silica plates (Merck's "Kieselgel 60F-254" —trade mark), 0.25 mm. thickness eluting with a mixture of diethyl ether, methanol and formic acid in the proportion 95:4:1 by volume; or (o) for those compounds wherein $R^1$ has any of the meanings stated above except a hydrogen atom the reaction of the corresponding compound of the formula I wherein $R^1$ is a hydrogen atom with an alkylating agent of the formula $R^1Z$, wherein Z has the meaning defined above and $R^1$ has any of the meanings stated above except a hydrogen atom.

The micro-organism *S. longisporoflavus* NCIB 11426, which is used in process (p) above is a known microorganism which is available to the public without any restriction, upon payment of any required fee, from the National Collection of Industrial Bacteria, Ministry of Agriculture, Fisheries and Food, Torry Research Station, 135 Abbey Road, Aberdeen AB9 8DG, Scotland.

As stated above, the compounds have the effect of increasing the proportion of propionic acid in rumen fluid, and in particular increase the proportion of propionic acid at the expense of methane and/or acetic acid. This is known to be a desirable effect in ruminant nutrition, because propionic acid is a much more efficient precursor of glucose, from which the animal derives its energy and growth, than is acetic acid; while that part of the animals' food intake which is converted to methane is simply lost to the animal, the methane being excreted by eructation. Thus, the modification of rumen metabolism achieved by the compounds of the invention is a most useful effect, and is believed to increase the rate of growth and the food conversion efficiency of ruminant animals.

Thus, according to a further feature of the invention there is provided a method for use in the husbandry of domestic ruminant animals, for increasing the efficiency of their food conversion, which comprises orally administering to the animals a compound of the invention as described above.

In the method of the invention, the compounds of the invention are preferably orally administered to the animals as a supplement to their normal diet, that is to say, in admixture with salt-licks, dissolved in the drinking water or, for young animals such as lambs or calves, dissolved in whole milk or skim milk. The compounds of the invention are incorporated into food, feedblocks, salt-licks, drinking water, whole milk and skim milk to such an extent that each treated animal will ingest from 0.01 mg./kg. body weight to 30 mg./kg. body weight per day, preferably from 0.01 mg./kg. to 10 mg./kg. per day, of a compound of the invention.

The compounds of the invention may alternatively be orally administered to animals in the form of a slow-release, intra-ruminal pellet or bolus, such that the animal will absorb a similar quantity per day of a compound of the invention.

The animals may receive the compound of the invention for substantially the whole of their growing period, or for only a part of their growing period, for example the early part and/or the period leading up to slaughter. The increase in growth rate achieved by practising the method of the invention enables animals reared for meat to be brought to market weight or slaughter weight in a shorter growing period than normal or it enables heavier animals to be produced at the end of the normal growing period. The improved efficiency of food conversion achieved by practising the method of the invention enables treated animals to reach any desired weight while consuming less food than untreated animals grown to the same weight. At optimum growth promoting inclusion levels, no indication of any toxic effect due to the compounds of the invention is observed.

According to a further feature of the invention, there is provided a composition which comprises a compound of the invention, together with a solid or liquid, edible non-toxic diluent or carrier.

A suitable liquid diluent or carrier is, for example, drinking water, whole milk or skim milk.

A suitable solid, edible, non-toxic diluent or carrier may be, for example, a conventional nutritionally balanced ruminant feedstuff, for example a typical cattle or sheep diet consisting of cereal products, such as barley meal, maize meal or wheat feed, nut and seed products, such as decorticated ground nut cake or cotton seed cake, or extracted cotton seed cake, together with minor amounts of, for example feather meal, seaweed meal, bone meal, bone flour, chalk, salt, urea, molasses, vitamines and trace minerals; or it may be an inert solid diluent or carrier of no energy value, for example kaolin, talc, calcium carbonate, fuller's earth, attapulgus clay, ground oyster shells or ground limestone; or it may be starch or lactose.

The composition of the invention may take the form of a supplemented feedstuff for direct feeding to animals, in which case it will contain from 5 ppm to 3000 ppm of the compound of the invention in admixture with a conventional ruminant feedstuff; or it may take the form of a concentrated premix for dilution with a conventional ruminant feedstuff to produce a supplemented feedstuff suitable for direct feeding, and such a premix will contain from 0.3% w/w to 50% w/w of the compound of the invention in admixture with either a conventional, nutritionally balanced ruminant feedstuff, an inert solid diluent of no energy value, for example ground limestone, or starch or lactose.

According to a further feature of the invention there is provided a process for the manufacture of a solid composition of the invention which comprises uniformly mixing a compound of the invention with a solid, edible, non-toxic diluent or carrier.

The compound of the formula I is preferably serially diluted with the diluent or carrier in two or more successive stages, to ensure even mixing.

The invention is illustrated, but not limited, by the following Examples:

EXAMPLE 1

M.139603 (1.0 g.) was dissolved in dichloromethane (40 ml.), acetyl chloride (5 ml.) was then added and the mixture allowed to stand in a stoppered flask at room temperature over the weekend. The solution was then filtered and the filtrate was evaporated to dryness. The resulting gum was examined on thin layer chromatography (TLC), which showed that approximately 90% of a new product had formed. The gum was dissolved in a little acetone and spread onto two preparative TLC plates (Merck ART 5717—40 cm.×20 cm.×2 mm) which were developed in chloroform/methanol/formic acid (90:5:5). Two bands $R_F=0.46$ and $0.54$ were removed from the plate and eluted with ethyl acetate/methanol (95:5) to give respectively 490 mg. of a new product, and 320 mg. of a mixture of the new product and the starting material, M.139,603. The mixed material of $R_f=0.46$ was repurified in a similar manner to give 192 mg. of single spot product; this material was combined with the previously eluted product to give a total of 682 mg. of M.139,603 acetate, having the NMR spectrum, in deuterochloroform as shown in FIG. 1.

In a similar manner, using 2-bromobenzoyl chloride in place of acetyl chloride, there was obtained:

M.139,603 2-bromobenzoate (I, $R^1=CH_3$, $R^2=CH_2O.CO(2-BrC_6H_4)$). Analysis: Calculated for $C_{42}H_{56}O_9BrNa.2H_2O$: C, 59.8; H, 7.1%. Found C, 59.7; H, 6.8%. Accurate mass measurement of mass spectrum molecular ion: calculated for $C_{42}H_{56}O_9{}^{79}BrNa$: 806.2988; Found: 806.3006.

EXAMPLE 2

To a stirred solution of the sodium salt of M.139,603 (0.624 g., 1.0 mmole) in methylene chloride (2.0 ml.) was added ethoxalyl chloride (0.5 ml. 4.5 mmole), and the mixture was stirred at room temperature for 64 hours. The solvent was evaporated under reduced pressure and the residue was treated with 50% aqueous ethanol containing sodium hydrogen carbonate to destroy the excess acid chloride. This mixture was diluted with water and extracted twice with ether, and the combined ether extracts were washed with water, dried (anhydrous magnesium sulphate) and concentrated to dryness under reduced pressure. The residue was chromatographed on silica gel (Merck 7734) using toluene-acetone (4:1) as eluant. Evaporation of the appropriate fractions gave the ethoxalyl ester of M.139,603 (I, $R^1=CH_3$, $R^2=CH_2O.CO.COOC_2H_5$) as a white froth. Calculated for $C_{39}H_{57}O_{11}Na$: C, 64.6, H, 7.9%. Found C,64.8; H, 8.1%. Accurate mass measurment of mass spectrum molecular ion: Calculated for $C_{39}H_{57}O_{11}Na$: 724.3799; found: 724.3796.

In a similar manner, the following ester derivatives of M.139,603 were prepared from the sodium salt of M.139,603 and the appropriate acid halide. Structures were confirmed by accurate mass measurement of the mass spectrum molecular ion.

| $R^2$ | Accurate Mass Measurement of molecular ion | Analysis |
|---|---|---|
| —$CH_2O.CO.CH_2Br^1$ | Calculated for $C_{37}H_{54}{}^{79}BrO_9Na$ 744.2850 Found: 744.2791 | Calculated for $C_{37}H_{54}BrO_9Na$: C, 59.6; H, 7.2; Br, 10.7%. Found: C, 59.9; H, 7.5; Br, 9.9%. |

| $R^2$ | Accurate Mass Measurement of molecular ion | Analysis |
|---|---|---|
| —$CH_2O.CO.CH_2Cl$[2] | Calculated for $C_{37}H_{54}{}^{35}ClO_9Na$ 700.3354 Found: 700.3383 | Calculated for $C_{37}H_{54}ClO_9Na$: C, 63.4; H, 7.7; Cl, 5.1%. Found: C, 63.0; H, 7.8; Cl, 5.4% |
| —$CH_2O.CO.C_6H_5$[2] | Calculated for $C_{42}H_{57}O_9Na$ 728.3901 Found: 728.3938 | Calculated for $C_{42}H_{57}O_9Na$: ½$H_2O$ C, 68.4; H, 7.9%. Found: C, 68.5; H, 7.8%. |

Footnotes
[1]Used 6.0 equivalents of acid chloride.
[2]Used 3.8 equivalents of acid chloride, and stirred at room temperature for 20 hours.

EXAMPLE 3

To a stirred solution of the sodium salt of M.139,603 (1.0 g., 1.60 mmole) in toluene (10 ml.) was added succinic anhydride (0.18 g. 1.8 mmole) and triethylamine (0.26 ml., 1.9 mmole). The mixture was heated at reflux temperature for 20 hours, then cooled, and the solvent was evaporated under reduced pressure. The residual gum was dissolved in ether (100 ml.) and the solution was extracted with saturated sodium carbonate solution (2×100 ml.). The combined aqueous extracts were acidified with 2 N hydrochloric acid and extracted with ether (2×70 ml.), and the combined ether extracts were dried (anhydrous magnesium sulphate) and concentrated under reduced pressure. The residual gum was purified by chromatography on silica gel (Merck 7734) using ethyl acetate as eluant. The appropriate fractions were combined and concentrated under reduced pressure to give the monosuccinyl ester of M.139,603 (I, $R^1=CH_3$, $R^2=CH_2O.CO.CH_2CH_2COOH$) as a white froth. Analysis: Calculated for $C_{39}H_{57}O_{11}Na^2H_2O$: C, 61.6; H, 8.0%. Found: C, 61.3; H, 7.8%. Accurate mass measurement of mass spectrum molecular ion: calculated for $C_{39}H_{57}O_{11}Na$ 724.3799; found 724.3810.

EXAMPLE 4

To a stirred solution of the sodium salt of M.139,603 (312 mg., 0.5 mmole) in toluene (2 ml.) was added methyl isocyanate (0.18 ml., 3.0 mmole) and, after heating the solution at 100° for 2 hours, the solvent was evaporated under reduced pressure. The residue was purified by chromatography on silica gel (Merck 7734) using ethyl acetate as eluant. The appropriate fractions were combined, and concentrated under reduced pressure to give the N-methylcarbamoyl ester of M.139,603 (I, $R^1$=N-methylcarbamoyl ester of M.139,603 (I, $R^1=CH_3$, $R^2=CH_2O.CONH.CH_3$) as a white froth. Analysis: Calculated for $C_{37}H_{56}NO_9Na1\frac{1}{2}H_2O$; C, 62.7; H, 8.3; N, 2.0%. Found: C, 62.7; H, 8.3; N, 1.8%. Accurate mass measurement of mass spectrum molecular ion: calculated for $C_{37}H_{56}NO_9Na$ 681.3853; found 681.3825.

In the similar manner, the following urethane and thiourethane derivatives of M.139,603 were prepared from the sodium salt of M.139,603 and the appropriate isocyanate or isothiocyanate. Structures were confirmed by accurate mass measurement of the mass spectrum molecular ion.

| $R^2$ | Accurate Mass Measurement of molecular ion | Analysis |
|---|---|---|
| —$CH_2O.CS.NH.CH_3$[1,2] | | Calculated for $C_{37}H_{56}NO_8SNa$: C, 62.8; H, 7.9; N, 2.0; S, 4.5%. Found: C, 62.8; H, 8.0; N, 1.8; S, 4.1% |
| —$CH_2O.CO.NH(CH_2)_3CH_3$[2] | Calculated for $C_{40}H_{62}NO_9Na$: 723.4310 Found: 723.4323 | Calculated for $C_{40}H_{62}NO_9Na$: C, 66.4; H, 8.6; N, 1.9%. Found: C, 66.0; H, 8.8; N, 2.3%. |
| —$CH_2O.CO.NH$—⟨⟩—$Br$[3,4] | | Calculated for $C_{42}H_{57}NO_9BrNa\frac{1}{2}H_2O$: C, 60.6; H, 7.0; N, 1.7; Br, 9.6%. Found: C, 60.3; H, 6.8; N, 1.6; Br, 9.7% |

Footnotes
[1]Used 7 equivalents of isocyanate
[2]Heated at 100° for 18 hours
[3]Used 1.2 equivalents of cyanate
[4]Stirred at room temperature for 4 days.

EXAMPLE 5

M.139,603 (95 mg.) was dissolved in ethyl acetate (10 ml.) and phenyl isocyanate (30 μl.) added. The course of the reaction was followed by TLC and was shown to be essentially complete after standing overnight.

The solution was then spread onto a preparative TLC plate (Merck ART 5717, 20 cm.×20 cm.×2 mm.) and developed in chloroform/methanol/formic acid (90:5:5). Two bands, $R_F$=0.48 and 0.58 were removed and eluted from the silica with ethyl acetate/methanol (95:5). Evaporation to dryness of the band, $R_F$=0.58 containing the product, gave a colourless gum weighing 87 mg. which was then crystallised from ether to give the N-phenylcarbamoyl ester of M.139,603 (I, $R^1=CH_3$, $R^2=CH_2O.CO.NHPh$), initially melting at 160°–165° C., then resolidifying, and remelting at 203°–205° C.

EXAMPLE 6

To a stirred suspension of sodium hydride (0.05 g., 2.1 mmole) in dry dimethylformamide in (20 ml.) and under an atmosphere of argon was added the sodium salt of M.139,603 (0.624 g., 1.0 mmole). After stirring for 1 hour at room temperature, methyl iodide (0.14 ml., 2.2 mmole) was added and stirring was continued for a further 2 hours. The reaction mixture was poured into water (100 ml.) and the aqueous solution extracted with ether (2×50 ml.). The combined ether extracts were washed with water (2×50 ml.), dried (anhydrous magnesium sulphate) and concentrated under reduced pressure to give an oil which solidified on standing. Further drying under reduced pressure gave M.139,603 methyl ether (I, $R^1=CH_3$, $R^2=CH_2OCH_3$) as a white froth. Analysis: Calculated for $C_{36}H_{55}O_8Na1H_2O$: C, 65.9; H, 8.7%. Found: C, 66.1; H, 9.0% Accurate mass measurement of mass spectrum molecular ion: calculated for $C_{36}H_{55}O_8Na$ 638.3795; found 638.3795.

In a similar manner, the following ether and carbonate derivatives of M.139,603 were prepared from the sodium salt of M.139,603 and the appropriate alkyl, alkynyl or aryl bromide. Extractions were performed using ethyl acetate instead of ether and the products were further purified by chromatography on silica gel (Merck 7734) using ethyl acetate as the eluant. Structures were confirmed by accurate mass measurement of the mass spectrum molecular ion.

(40 ml.) was added activated manganese dioxide (3.2 g.). After stirring for 20 hours at room temperature, the reaction mixture was filtered and the filtrate was concentrated to dryness under reduced pressure. The residue was chromatographed on silica gel (Merck 7734) using ethyl acetate as the eluant and the appropriate fractions were concentrated under reduced pressure to give M.139,603 aldehyde (I, $R^1=CH_3$, $R^2=CHO$) as a white froth. Analysis: Calculated for $C_{35}H_{51}O_8NaH_2O$. C, 65.6; H, 8.3%. Found: C, 65.9; H, 8.5%. Accurate mass measurement of mass spectrum molecular ion: calculated for $C_{35}H_{51}O_8Na$ 622.3482; found 622.3431.

EXAMPLE 8

To a stirred solution of the sodium salt of M.139,603 aldehyde (0.10 g., 0.16 mmole) in ethanol (5 ml.) was added sodium acetate (0.10 g., 1.22 mmole) and hydroxylamine hydrochloride (0.10 g., 1.44 mmole). The mixture was heated at reflux for ½ hour, cooled and filtered, and the filtrate was concentrated to dryness under reduced pressure. The residue was chromatographed on silica gel (Merck 7734—trade mark) using acetone/6-0°-80° petroleum ether (1:1) as eluant, and the appropriate fractions were concentrated under reduced pressure to give M.139,603 aldehyde oxime (I, $R^1=CH_3$, $R^2=CH=NOH$) as a froth. Analysis: Calculated for $C_{35}H_{52}O_8NNa\frac{1}{2}H_2O$ C, 65.0; H, 8.2; N, 2.2%. Found C, 65.1; H, 8.6; N, 2.3%. Accurate mass measurement of mass spectrum molecular ion: calculated for

| $R^2$ | Accurate Mass Measurement of molecular ion | Analysis |
|---|---|---|
| $-CH_2OCH_2.C_6H_5$ | Calculated for $C_{42}H_{59}O_8Na$: 714.4108 Found: 714.4118 | Calculated for $C_{42}H_{59}O_8Na$ 1.5$H_2O$ C, 68.0; H, 8.4%. Found: C, 68.0; H, 8.4%. Found: C, 68.1; H, 8.6% |
| $-CH_2OCH_2.C\equiv CH$ | Calculated for $C_{38}H_{55}O_8Na$: 662.3795 Found: 662.3788 | Calculated for $C_{38}H_{55}O_8Na$ 0.5$H_2O$ C, 68.0; H, 813%. Found: C, 68.3; H, 8.5% |
| $-CH_2O(CH_2)_3CH_3$ | Calculated for $C_{39}H_{61}O_8Na$: 680.4265 Found: 680.4260 | Calculated for $C_{39}H_{61}O_8Na$ 0.5$H_2O$ C, 67.9, H, 9.0% Found: C, 68.3; H, 9.1% |
| 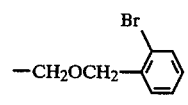 | Calculated for $C_{42}H_{58}{}^{79}BrO_8Na$: 792.3203 Found: 792.3214 | Calculated for $C_{42}H_{58}BrO_8Na$ 2.5$H_2O$ C, 60.1; H, 7.5; Br, 9.5%. Found: C, 60.2; H, 7.0; Br. 9.8% |
| $-CH_2O.CO.OC_2H_5$ | Calculated for $C_{38}H_{57}O_{10}Na$: 696.3898 Found: 696.3850 | Calculated for $C_{38}H_{57}O_{10}Na$ 1$H_2O$ C, 63.9; H, 8.3%. Found: C, 63.8; H, 8.2% |
| $-CH_2O(CH_2)_2N(CH_3)_2{}^1$ | Calculated for $C_{39}H_{62}NO_8Na$: 695.4342 Found: 695.4373 | Calculated for $C_{39}H_{62}NO_8Na$ 2.5$H_2O$ C, 63.2; H, 9.0; N, 1.9%. Found: C, 63.4; H, 8.5; N, 1.7% |

Footnote
[1]Eluted from silica with methylene chloride/methanol (9:1).

EXAMPLE 7

To a stirred solution of the sodium salt of M.139,603 (0.40 g., 0.64 mmole) in petroleum ether (b.p. 60°-80°)

$C_{35}H_{52}O_8NNa$ 637.3561; found 637.3591.

EXAMPLE 9

Mother liquors from the crystallisation of M.139,603, obtained from the fermentation of *Streptomyces longisporoflavus* NCIB 11426 as described in U.K. patent specification No. 2027013A, were chromatographed on preparative thin layer chromatography (P.T.L.C.) plates (Merck ART 5717, 40 cm.×20 cm.×2 mm.) using ether/glacial acetic acid (98.2) as the eluant. The band at $R_F=0.40$, corresponding to M.139,603, was discarded, but a second band at $R_F=0.23$ was removed from the plates and eluted with ethyl acetate/methanol (95:5) to give a viscous brown oil. This material was further purified by repeating the P.T.L.C. using the solvent system chloroform/methanol/formic acid (90:5:5). The band, $R_F=0.33$, was removed from the plates, and the product, demethyl—M.139,603 (I, $R^1=H$, $R^2=CH_2OH$), was crystallised from petroleum ether (b.p. 60°-80° C.), m.p. 156°-158° C.

EXAMPLE 10

Premixes suitable for dilution with an animal feedstuff may be manufactured by incorporating 10, 25, 50, 100 or 250 mg. of the ethoxalyl ester of M.139,603 in ground limestone so that the final weight of the premix is 500 g.

Similar premixes may be manufactured using equivalent quantities of any other compound of the invention.

EXAMPLE 11

An animal feedstuff suitable for direct feeding to ruminants may be manufactured by intimately mixing 500 g. of a premix, obtained as described in Example 10, with 999.5 mg. of a typical cattle feedstuff, to obtain a ruminant feedstuff containing 10, 25, 50, 100 or 250 g. of the ethoxalyl ester of M.139,603, or any other compound of the invention, per metric ton, according to the concentration of the active ingredient in the premix used.

Suitable cattle feedingstuffs are:

|  | cwt | kg |
|---|---|---|
| Dairy Cake | | |
| Barley meal | 10¼ | 512.5 |
| Maize meal | 1 | 50 |
| Decorticated ground nut cake | 1 | 50 |
| Decorticated cotton seed cake | 1 | 50 |
| Extracted cotton seed cake | 1 | 50 |
| Wheat feed | 3 | 150 |
| Feather meal | ¼ | 12.5 |
| Seaweed meal | ¼ | 12.5 |
| Bone meal | ¼ | 12.5 |
| Chalk | ¼ | 12.5 |
| Molasses | 1½ | 75 |
| Vitamins and trace mineral mix | ¼ | 12.5 |
|  | 20 | 1000.0 |
| Beef Cube | | |
| Barley meal | 11 | 550 |
| Wheat feed | 5¼ | 262.5 |
| Decorticated ground nut cake | ¼ | 12.5 |
| Extracted ground nut cake | 42 lbs. | 18.75 |
| Bone flour | ¼ | 12.5 |
| Chalk | 42 lbs. | 18.75 |
| Salt | 14 lbs. | 6.25 |
| Molasses | 2 | 12.5 |
| Urea | ¼ | 12.5 |
| Vitamins and trace mineral mix | 14 lbs. | 6.25 |
|  | 20 cwt. | 1000.00 |

EXAMPLE 12

The ability of a compound of the invention to inhibit the production of methane in the rumen of ruminant animals, and to increase the proportion of propionate to acetate and butyrate (P/A+B) in the volatile fatty acids (VFA) produced, without at the same time depressing the overall digestive process, is demonstrated as follows:

Rumen fluid is collected on a regular basis from two steers, which are fed on the same hay-plus-concentrate diet. Sampling time is standarised as for as possible, and the fluid from the two animals is pooled on a 50/50 basis. Large particulate matter is removed by filtering the pooled fluid through four layers of muslin cloth. The filtrate is then diluted in the ratio of one volume of filtrate to three volumes of an artificial rumen fluid (prepared as described by G. L. Bales et al., Journal of Dairy Science, 1976, volume 59, page 1850, but omitting acetic acid), and the pH of the mixture is adjusted to 6.9-7.0 with saturated aqueous sodium carbonate solution. Aliquots (50 ml.) of this mixture are dispensed into 100 ml. conical flasks containing dried ground hay (0.5 g.), and each flask is used to test a test compound at a particular concentration.

The test compound is added to the conical flask as a solution in ethanol, the flask is flushed with carbon dioxide gas, stoppered with a suba-seal, and incubated at 39° C. for 15-16 hours. After one hour, a narrow bore needle is inserted through the suba-seal to relieve the gas pressure, and the need is withdrawn 30 minutes before the incubation is ended. Fermentation is then stopped by placing the flask in ice, and after 15 minutes cooling, the gas over the liquid is analysed for methane by gas chromatography. The flask contents are then filtered through a previously dried and weighed sintered glass funnel, the funnel is oven-dried and, by difference, the weight of hay digested is determined. (Blank flasks containing no hay are treated similarly to determine non-cellulose residue). Three samples of the filtrate are analysed by gas chromatography for VFAs, and by comparison with the previously determined, pre-incubation level of VFAs, the net VFAs (acetate, propionate and butyrate) produced during the incubation is determined.

The following results were obtained (a negative control in which no test compound is employed is also included):

|  |  | 3 μg./ml. | | 30 μg./ml. | |
|---|---|---|---|---|---|
| $R^1$ | $R^2$ | Methane % of control | P/A + B % of control | Methane % of control | P/A + B % of control |
| $CH_3$ | $CH_2O.COCH_3$ | 66 | 128 | — | — |
| $CH_3$ | $CH_2O.COPh$ | 71 | 168 | — | — |
| $CH_3$ | $CH_2O.CO(2-Br.C_6H_4)$ | 81 | 158 | — | — |
| $CH_3$ | $CH_2O.CO.COOC_2H_5$ | 25 | 170 | — | — |
| $CH_3$ | $CH_2O.CO.CH_2Br$ | 41 | 141 | — | — |

-continued

| R¹ | R² | 3 µg./ml. Methane % of control | 3 µg./ml. P/A + B % of control | 30 µg./ml. Methane % of control | 30 µg./ml. P/A + B % of control |
|---|---|---|---|---|---|
| $CH_3$ | $CH_2O.CO.CH_2Cl$ | 34 | 152 | — | — |
| $CH_3$ | $CH_2O.CO(CH)_2COOH$ | 85 | 117 | 63 | 121 |
| $CH_3$ | $CH_2O.CO.NH.CH_3$ | 46 | 146 | — | — |
| $CH_3$ | $CH_2O.CS.NH.CH_3$ | 47 | 146 | — | — |
| $CH_3$ | $CH_2O.CO.NH(CH_2)_3CH_3$ | 57 | 132 | — | — |
| $CH_3$ | $CH_2O.CO.NH(4\text{-}Br.C_6H_4)$ | 76 | 119 | 61 | 138 |
| $CH_3$ | $CH_2O.CO.NHPh$ | 82 | 121 | 49 | 138 |
| $CH_3$ | $CH_2OCH_3$ | 27 | 164 | — | — |
| $CH_3$ | $CH_2OCH_2Ph$ | 54 | 140 | — | — |
| $CH_3$ | $CH_2OCH_2.C{\equiv}CH$ | 21 | 145 | — | — |
| $CH_3$ | $CH_2O(CH_2)_3CH_3$ | 64 | 133 | — | — |
| $CH_3$ | $CH_2OCH_2(2\text{-}Br.C_6H_4)$ | 89 | 122 | 56 | 153 |
| $CH_3$ | $CHO$ | 48 | 140 | — | — |
| $H$ | $CH_2OH$ | 65 | 126 | — | — |

What we claim is:

1. A derivative of M.139,603 of the formula:

wherein:

$M^+$ is an alkali metal, alkaline earth metal, ammonium, alkylammonium or hydroxyalkylammonium cation;

$R^1$ is a hydrogen atom, an alkyl radical or an optionally substituted phenylalkyl radical; and $R^2$ is a formyl, iminomethyl, hydroxyiminomethyl or aminomethyl radical, or a radical of the formula —$CH{:}NR^3$, —$CH{:}NOR^4$ or —$CH_2NR^5R^6$ wherein $R^3$, $R^4$, $R^5$ and $R^6$ may each be an alkyl or an optionally substituted phenyl or phenylalkyl radical; or a radical of the formula —$CH_2OR^7$ wherein $R^7$ is an alkyl, alkenyl, alkynyl, alkoxycarbonyl or alkylaminoalkyl radical or an optionally substituted phenylalkyl radical; or a radical of the formula —$CH_2O.COR^8$ wherein $R^8$ is an alkyl, cycloalkyl, (cycloalkyl)alkyl, halogenoalkyl, hydroxyalkyl, alkoxyalkyl, aminoalkyl, mono- or di-alkylaminoalkyl, alkoxycarbonylalkyl, carboxyalkyl, carbamoylalkyl, N-alkylcarbamoylalkyl, N,N-dialkylcarbamoylalkyl or optionally substituted phenyl, naphthyl or phenylalkyl radical; or a radical of the formula —$CH_2O.CO.COR^9$ wherein $R^9$ is an amino, mono- or di-alkylamino, alkoxy or optionally substituted phenyl, naphthyl or phenylalkyl radical; or a radical of the formula —$CH_2O.CX.NR^{10}R^{11}$ wherein X is an oxygen or sulphur atom and $R^{10}$ and $R^{11}$, which may be the same or different, are each a hydrogen atom, an alkyl radical or an optionally substituted phenyl, naphthyl or phenylalkyl radical; or, when $R^1$ is a hydrogen atom or an alkyl radical of 2 or more carbon atoms or an optionally substituted phenylalkyl radical, $R^2$ is a hydroxymethyl radical, and wherein each alkyl, alkenyl or alkynyl radical contains up to 6 carbon atoms, and wherein, in each complex radical containing an alkyl part, the said alkyl part contains 1 to 6 carbon atoms, and wherein each cycloalkyl radical or cycloalkyl part of a (cycloalkyl)alkyl radical contains 3 to 7 carbon atoms and wherein the optional substituent in the optionally substituted phenyl, naphthyl or phenylalkyl radical is a halogen atom, a nitro, cyano or hydroxy radical, or an alkyl, alkoxy, halogenoalkyl, halogenoalkoxy, alkylamino, dialkylamino or alkanoylamino radical of up to 8 carbon atoms.

2. A derivative as claimed in claim 1 wherein any of $R^1$, $R^3$, $R^4$, $R^5$, $R^6$, $R^7$, $R^8$, $R^9$, $R^{10}$ or $R^{11}$ is an alkyl radical of 1 to 3 carbon atoms or is a complex radical containing an alkyl part which contains 1 to 3 carbon atoms or $R^7$ is an alkenyl or alkynyl radical of 2 or 3 carbon atoms.

3. A derivative as claimed in claim 1 wherein $M^+$ is a sodium, lithium, potassium, calcium, magnesium, zinc, ammonium, mono-, di-, tri- or tetraalkylammonium ion wherein each alkyl is of 1 to 10 carbon atoms, or mono-, di- or tri-(hydroxyalkyl)ammonium ion wherein each hydroxyalkyl is of 1 to 10 carbon atoms.

4. A compound as claimed in claim 1 wherein:
$R^1$ is hydrogen and $R^2$ is hydroxymethyl;
$R^1$ is methyl and $R^2$ is formyl;
$R^1$ is methyl and $R^2$ is methoxymethyl;
$R^1$ is methyl and $R^2$ is propargyloxymethyl;
$R^1$ is methyl and $R^2$ is benzoyloxymethyl;
$R^1$ is methyl and $R^2$ is 2-bromobenzoyloxymethyl;
$R^1$ is methyl and $R^2$ is chloroacetoxymethyl;
$R^1$ is methyl and $R^2$ is ethoxalyloxymethyl; or
$R^1$ is methyl and $R^2$ is N-methylthiocarbamoyloxymethyl.

5. A composition which comprises a derivative of M.139,603 as claimed in claim 1 together with a solid or liquid edible non-toxic diluent or carrier.

6. A method for use in the husbandry of domestic ruminant animals for increasing the efficiency of their food conversion, which comprises orally administering to the animals a derivative of M.139,603 as claimed in claim 1.

* * * * *